US012685783B2

(12) United States Patent
Cai et al.

(10) Patent No.: US 12,685,783 B2
(45) Date of Patent: Jul. 21, 2026

(54) MOLECULAR SELF-ASSEMBLED NANOPARTICLES AND PREPARATION METHOD AND APPLICATION THEREOF

(71) Applicant: AIR FORCE MEDICAL UNIVERSITY, Xi'an (CN)

(72) Inventors: Bolei Cai, Xi'an (CN); Liang Kong, Xi'an (CN); Feng Cao, Xi'an (CN); Fuwei Liu, Xi'an (CN); Le Wang, Xi'an (CN); Yunpeng Li, Xi'an (CN); Taiqiang Dai, Xi'an (CN); Han Bao, Xi'an (CN)

(73) Assignee: AIR FORCE MEDICAL UNIVERSITY, Xi'an (CN)

( * ) Notice: Subject to any disclaimer, the term of this patent is extended or adjusted under 35 U.S.C. 154(b) by 351 days.

(21) Appl. No.: 18/364,882

(22) Filed: Aug. 3, 2023

(65) Prior Publication Data

US 2024/0207437 A1 Jun. 27, 2024

(30) Foreign Application Priority Data

Dec. 26, 2022 (CN) ......................... 202211675321.2

(51) Int. Cl.
*A61K 47/55* (2017.01)
*A61K 9/51* (2006.01)
*A61K 47/54* (2017.01)
*A61K 47/69* (2017.01)
*A61P 19/02* (2006.01)

(52) U.S. Cl.
CPC ........ *A61K 47/6901* (2017.08); *A61K 9/5192* (2013.01); *A61K 47/542* (2017.08); *A61K 47/6935* (2017.08); *A61P 19/02* (2018.01)

(58) Field of Classification Search
None
See application file for complete search history.

(56) References Cited

FOREIGN PATENT DOCUMENTS

| | | |
|---|---|---|
| CN | 112807288 A | 5/2021 |
| CN | 114099466 A | 3/2022 |

OTHER PUBLICATIONS

Chong et al.; Advances in fabricating double-emulsion droplets and their biomedical applications, 2015; Microfluid Nanofluid, vol. 19, pp. 1071-1090. (Year: 2015).*

Ternant et al.; "Clinical Pharmacokinetics and Pharmacodynamics of Monoclonal Antibodies Approved to Treat Rheumatoid Arthritis," 2015; Clin Pharmacokinet, vol. 54, pp. 1107-1123. (Year: 2015).*

Goto et al., editors; "Application of Ionic Liquids in Drug Delivery," 2021, Springer; pp. 1-242. (Year: 2021).*

Zavgorodnya et al.; "Polyethylene glycol derivatization of the non-active ion in active pharmaceutical ingredient ionic liquids enhances transdermal delivery," RSC, New J Chem, vol. 41, pp. 1499-1508. (Year: 2017).*

Akkad et al.; "Degradable Polymers and Nanoparticles Built from Salicylic Acid," 2018, WILEY-VCH, Macromol. Rapid Commun., vol. 39, No. 1800182, pp. 1-5. (Year: 2018).*

Kang et al.; "Nanoparticles Coated with Neutrophil Membranes Can Effectively Treat Cancer Metastasis," 2017, ACS; ACSNano, vol. 11, pp. 1397-1411. (Year: 2017).*

Notice of first Office action dated May 16, 2024 in SIPO application No. 202211675321.2.

Retrieval report—First search dated May 15, 2024 in SIPO application No. 202211675321.2.

Notification to Grant Patent Right for Invention dated Aug. 22, 2024 in SIPO application No. 202211675321.2.

Retrieval report—Supplementary search dated Jul. 16, 2024 in SIPO application No. 2022116753212.

Xiao Chen, "Study on polyethylene glycol-aspirin sustained-release drug, Chinese Master's Theses Full-text Database Engineering Science and Technology," Jan. 15, 2013, pp. 1-43, No. 01 (Translation of Abstract provided. ) Claims involved: 1-8.

Xu Yisong et al., "Preparation and Applications in Organic Reactions of Polyethylene Glycol Functionalized Ionic Liquids," Progress in Chemistry, Oct. 15, 2015, pp. 1,400-1,412, vol. 27, No. 10. (Translation of Abstract provided.) DOI: 10. 7536 /PC150320 Claims involved: 1-8.

Qiangzhe Zhang et al., "Neutrophil membrane-coated nanoparticles inhibit synovial inflammation and alleviate joint damage in inflammatory arthritis," Nature Nanotechnology, Dec. 31, 2018, pp. 1182-1190, vol. 13; doi: 10.1038/s41565-018-0254-4/10.1038/s41565-018-0254-4 Claims involved: 1-8.

* cited by examiner

*Primary Examiner* — Tigabu Kassa
*Assistant Examiner* — Ivan A Greene
(74) *Attorney, Agent, or Firm* — Pilloff Passino & Cosenza LLP; Rachel Pilloff; Sean Passino

(57) ABSTRACT

Molecular self-assembled nanoparticles and a preparation method and application thereof are provided in the present application, relating to the technical field of precise treatment of arthritis. The molecular self-assembled nanoparticles include a neutrophil membrane and aspirin-functionalized polyethylene glycol (PEG) nanoparticles, where the neutrophil membrane is coated on a surface of the aspirin-functionalized PEG nanoparticles, and a mass ratio of the neutrophil membrane to the aspirin-functionalized PEG nanoparticles is 1:8.

3 Claims, 25 Drawing Sheets

S1

Reacting aspirin with a functionalized ionic liquid of PEG to obtain aspirin-functionalized PEG

S2

Dissolving the aspirin-functionalized PEG in an organic solvent to obtain a mixed solution, dropping the mixed solution into water, followed by ultrasonically centrifugation to obtain a precipitate as the aspirin-functionalized PEG nanoparticles Dissolving the aspirin-functionalized PEG nanoparticles in a phosphate buffer solution (PBS)

↓

Dropwise adding a neutrophil membrane solution, followed by ultrasonic treatment and ice bath treatment to obtain the molecular self-assembled nanoparticles

MOLECULAR SELF-ASSEMBLED NANOPARTICLES AND PREPARATION METHOD AND APPLICATION THEREOF

CROSS-REFERENCE TO RELATED APPLICATIONS

This application claims priority to Chinese Patent Application No. 202211675321.2, filed on Dec. 26, 2022, the contents of which are hereby incorporated by reference.

TECHNICAL FIELD

The present application relates to the technical field of precise treatment of arthritis, and in particular to molecular self-assembled nanoparticles, a preparation method and an application thereof.

BACKGROUND

Conventional methods for treating arthritis include surgery, radiation therapy and chemotherapy, which are generally hampered by complex cytokines involved in arthritis and diverse cytokine targets in clinical arthritis treatment, resulting in severe side effects, poor specificity and ineffective targeted drug delivery. Therefore, developing drugs with fewer side effects and greater effectiveness for precisely treating arthritis is an urgent need in the technological area of precision arthritis treatment.

SUMMARY

Based on the above contents, the present application provides molecular self-assembled nanoparticles, a preparation method and an application thereof.

To achieve the above objectives, the present application provides following technical schemes:

one technical scheme of the present application provides molecular self-assembled nanoparticles, including a neutrophil membrane and aspirin-functionalized polyethylene glycol (PEG) nanoparticles;

the neutrophil membrane is coated on a surface of the aspirin-functionalized PEG nanoparticles; and a mass ratio of the neutrophil membrane to the aspirin-functionalized PEG nanoparticles is 1:6-10.

Excessive amount of neutrophil membrane causes aggregation of the membrane, making it difficult to encapsulate aspirin-functionalized PEG nanoparticles; and insufficient amount of neutrophil membrane makes the encapsulation efficiency too low to achieve a required concentration system of the present application.

Optionally, a preparation method of the aspirin-functionalized PEG nanoparticles includes following steps:

reacting aspirin with a functionalized ionic liquid of PEG to obtain aspirin-functionalized PEG; and dissolving the aspirin-functionalized PEG in an organic solvent to obtain a mixed solution, dropwise adding the mixed solution into water, followed by ultrasonically centrifugation to obtain a precipitate as the aspirin-functionalized PEG nanoparticles.

Optionally, specific steps of preparing the aspirin-functionalized PEG include:

(1) preparation of oil phase: dissolving aspirin and PEG in a mixed solvent (mixed solvent of dichloromethane and ethyl acetate or mixed solvent of dichloromethane and acetone, where a volume ratio of dichloromethane to ethyl acetate is 0.25-9:1 and a volume ratio of dichloromethane to acetone is 0.25-9:1) to prepare a solution containing aspirin in a concentration of 10-50 milligrams per milliliter (mg/mL) and PEG in a concentration of 100-250 mg/mL, thus obtaining the oil phase;

(2) preparation of emulsion: adding the oil phase into a polyvinyl alcohol (PVA) aspirin saturated solution for emulsification, where a ratio of the oil phase to PVA aspirin saturated solution is 1:80-300, and the PVA aspirin saturated solution includes PVA in a concentration of 0.3-5% (g/mL); obtaining an oil in water (O/W) emulsion; and (3) development of aspirin-functionalized PEG: adding distilled water into the O/W emulsion, and stirring at a low speed at room temperature until the organic solvent is completely volatilized; standing for precipitation, removing supernatant, filtering and collecting on a filter, washing with distilled water for three times, and drying to obtain the aspirin-functionalized PEG.

In the step (2), a temperature of the PVA aspirin saturated solution is −10 degrees Celsius (° C.)-25° C., and an emulsification condition includes stirring at −10-25° C. and 800-1,800 revolutions per minute (rpm).

In the step (3), a stirring speed is 500 rpm, a stirring duration for stirring until the organic solvent is completely volatilized is 1-5 hours (h), and the drying includes drying in a drying dish under a room temperature, or freeze drying under a low temperature, or vacuum drying.

Optionally, the organic solvent is dimethyl sulfoxide (DMSO), and a mass-volume ratio of the aspirin-functionalized PEG to the organic solvent is 0.05 mg: 1 mL.

Optionally, a volume ratio of the mixed solution to the water is 1:2-4; and the centrifugation specifically includes centrifugation at 6,000 rpm for 5-10 min.

The conditions of centrifugation being limited to 6,000 rpm for 5-10 min contribute to the molecular self-assembly, and centrifugation in excess of those conditions illustrated above affects the proceeding of molecular self-assembly.

Another technical scheme of the present application provides a preparation method of the molecular self-assembled nanoparticles, including following steps:

dissolving the aspirin-functionalized PEG nanoparticles in a phosphate buffer solution (PBS), and then dropwise adding a neutrophil membrane solution, followed by ultrasonic treatment and ice bath treatment to obtain the molecular self-assembled nanoparticles.

Optionally, a power of the ultrasonic treatment is 80 Watts (W) and a duration is 1.5 min, and a duration of ice bath treatment is 5-15 seconds (s).

Optionally, a mass-volume ratio of the aspirin-functionalized PEG nanoparticles to the PBS is 0.05 mg: 1 mL.

Optionally, a concentration of the neutrophil membrane solution is 4 mg/mL, and a mass ratio of the neutrophil membrane in the neutrophil membrane solution to the aspirin-functionalized PEG nanoparticles is 1:6-10.

The neutrophil membrane is specified to a certain concentration and a certain amount to ensure a smooth encapsulation of aspirin-functionalized PEG nanoparticles by the neutrophil membrane, and a concentration and amount beyond the above-documented parameters lead to aggregation of the membrane or too low encapsulation efficiency, both of which will affect the encapsulation performance.

Another technical scheme of the present application provides an application of the molecular self-assembled nanoparticles in preparing targeted drugs for treating arthritis.

The technical concept of the present application is that:

the ameliorative effect of PEG alone on aspirin is less than optimal, and accelerated blood clearance occurs during the second injection, which further impairs the effects; after the particle is encapsulated by the cell membrane, the surface charge of the particle is neutralized to achieve good particle-to-particle dispersion, making it less likely to be adsorbed by vascular endothelial cells and recognized by immune cells in vivo, thus increasing drug utilization; neutrophils are one of the most common cells at the site of arthritis, with large amounts of lymphocyte function-associated antigen-1 (LFA-1) present on the surface of the polymorphonuclear neutrophils (PMN) membrane, and large amounts of intercellular adhesion molecule-1 (ICAM-1) protein expressed in activated cartilage tissues and cells; given to the antigen-antibody binding (ligand binding) of LFA-1 to ICAM-1 natively, the PMN membrane encapsulated drug is then better stored in the inflammation-activated cartilage tissue in a targeted manner. A reservoir system of molecularly self-assembled nanoparticles targeting site-specific for delivering drugs by using neutrophil membranes to encapsulate aspirin-functionalized PEG nanoparticles is constructed by the present application. Polymorphonuclear neutrophils membrane coated self-assembled poly salicylic acid (PMN-PSAs) particles prepared by the present application are engulfed by chondrocytes after being applied to the inflammation site, and the chondrocytes will slowly release aspirin monomer after engulfment and the content reaches its peak in about 6 days; the aspirin monomer released influences the inflammatory environment in the joint cavity, synovial inflammation, etc. to bring out the therapeutic effect, enabling the drug particles to have better bioavailability with better targeting and retention, and lower drug cost.

The present application discloses the following technical effects:

- the PMN-PSAs prepared by the present application reduces the total amount of drug used, decreases the effect on other sites and weakens the side effects caused by the drug, and provides better drug efficacy with high bioavailability, good targeting, and strong retention; also, the targeted effect helps to overcome the disadvantages of poor biocompatibility and the tendency of drug being confined by closed surface of plasma proteins in the circulatory system, as well as the ease of escape under the clearance mechanism of monocytes and macrophages in the reticuloendothelial system, thus improving its efficacy; and
- the preparation method of the present application is simple and easy for mass production.

BRIEF DESCRIPTION OF THE DRAWINGS

For a clearer description of the technical schemes in the embodiments of the present application or prior art, the following drawings are briefly described for use in the embodiments, and it is clear that the drawings in the following description are only some embodiments of the present application, and that other drawings are available to those of ordinary skill in the art without creative effort.

DETAILED DESCRIPTION OF THE EMBODIMENTS

Figure 1:
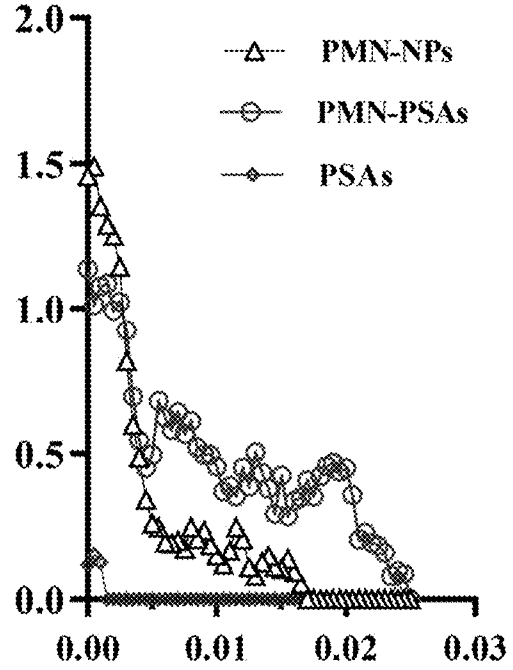
FIG. 1 is a diagram showing drug retention in inflammatory joints.

Various exemplary embodiments of the present application are now described in detail, and this detailed description should not be considered as a limitation of the present application, but should be understood as a further detailed description of certain aspects, features and embodiments of the present application.

It is to be understood that the terms described in the present application are intended to describe particular embodiments only and are not intended to limit the present application. Further, with respect to the range of values in the present application, it is to be understood that each intermediate value between the upper and lower limits of the range is also specifically disclosed. Each smaller range between any stated value or intermediate value within a stated range and any other stated value or intermediate value within a stated range is also included in the present application. The upper and lower limits of these smaller ranges may be independently included or excluded from the scope.

Unless otherwise indicated, all technical and scientific terms used herein have the same meaning as commonly understood by those of ordinary skill in the art described herein. Although the present application describes only preferred methods and materials, any methods and materials similar or equivalent to those described herein may also be used in the implementation or testing of the present application. All literature referred to in this specification is incorporated by reference for the purpose of disclosing and describing the methods and/or materials associated with the literature described. In the event of conflict with any incorporated literature, the contents of this specification shall prevail.

Without departing from the scope or spirit of the present application, various improvements and variations to specific embodiments of the specification of the present application are available, as will be apparent to those skilled in the art. Other embodiments obtained from the specification of the present application are obvious to the skilled person. The specification and embodiments of the present application are exemplary only.

The terms "including", "comprising", "having" and "containing" used in this specification are all open terms, which means including but not limited to.

The functionalized ionic liquid of polyethylene glycol (PEG) of the present application is prepared by the following steps: the compound containing polyether chain is esterified or halogenated by reagents such as methylsulfonyl chloride and sulfoxide chloride, and the esterified or halogenated polyether chain compound reacts with amine compounds (imidazole, pyridine, etc.) at one or both ends to form the corresponding PEG functionalized compound, and further functionalization of imidazole compounds is possible; anion or cation exchange is conducted to develop the corresponding functionalized ionic liquid of PEG. The method for preparing functionalized ionic liquid of PEG is a conventional technical means in the field and is not included in the contents protected by the present application, so it will not be repeated hereafter. The molecular weight of PEG used in this application is between 200 and 600; the properties of PEG vary with different molecular weights, from a colorless and odorless viscous liquid to a waxy solid. Those with molecular weights of 200-600 are liquid at room temperature, while those with molecular weights above 600 gradually become semi-solid, with the properties varying with different average molecular weights. As the molecular weight increases, the capacity of moisture absorption decreases accordingly. The product is soluble in water, ethanol and many other organic solvents, with a low vapor pressure and is stable against heat, acid and alkali, and does not interact with many chemicals. It has good hygroscopicity, lubricity and adhesion, with no toxicity and no stimulation. The average molecular weight of PEG used in the embodiments of the present application is 450.

The polymorphonuclear neutrophils (PMN) membrane described in the present application is extracted by PMN cell membrane extraction step using PMN membrane extraction kit; it is a conventional technical means in this field and is excluded from the protection scope of this application, which will not be repeated hereafter. The concentration of PMN membrane solution used in the embodiments of the present application is 4 milligrams per milliliter (mg/mL).

Unless otherwise specified, the raw materials used in the embodiments of the present application can be obtained from the purchase route.

Aspirin-functionalized PEG (A-PEG) in the embodiments of the present application is prepared by the following steps:

(1) preparation of oil phase: dissolving aspirin and PEG in a mixed solvent (mixed solvent with a volume ratio of dichloromethane to ethyl acetate of 5:1) to prepare a solution with a concentration of aspirin being 30 mg/mL and PEG being 200 mg/mL to obtain the oil phase;

(2) preparation of emulsion: adding the oil phase into a saturated solution of polyvinyl alcohol (PVA) aspirin for emulsification (stirring at 20° C. and 1,200 revolutions per minute (rpm)), where a volume ratio of the oil phase to the saturated solution of PVA aspirin is 1:150; obtaining an oil in water (O/W) emulsion; and (3) development of aspirin-functionalized PEG: adding distilled water into the O/W emulsion, and stirring at room temperature at 500 rpm until the organic solvent is completely volatilized; standing for precipitation, removing supernatant, filtering and collecting on a filter, washing with distilled water for three times, and drying in a drying dish at room temperature to obtain the aspirin-functionalized PEG (A-PEG).

The aspirin-functionalized PEG is prepared following a process with reaction formulas illustrated as follows:

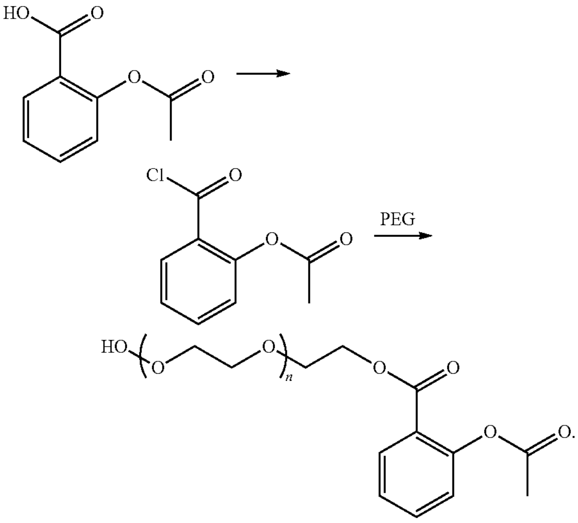

Figure 15:
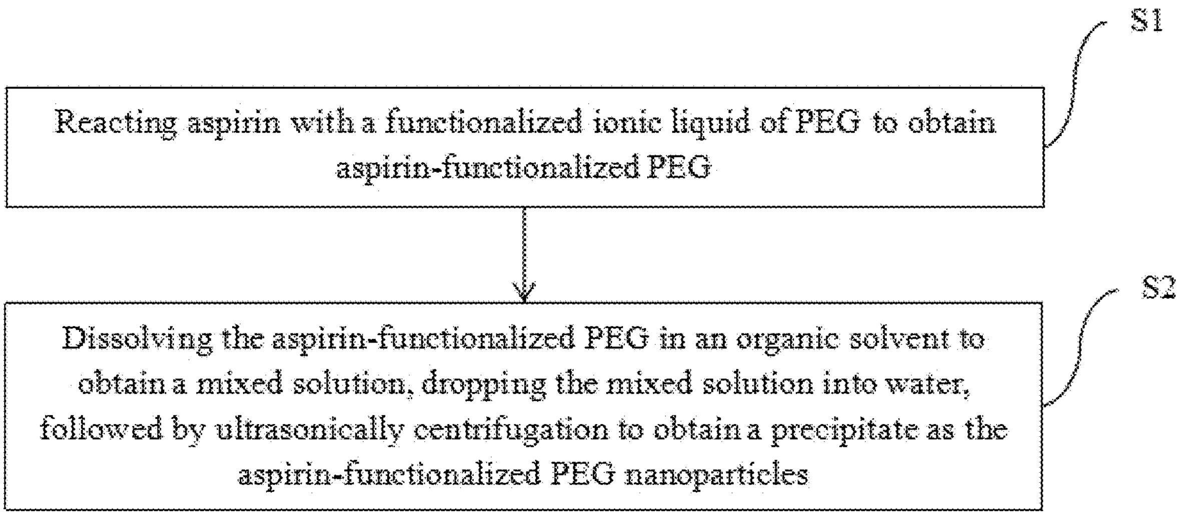
FIG. 15 is a process illustrating a preparation method of the aspirin-functionalized polyethylene glycol nanoparticles.

As shown in FIG. 15, a preparation method of the A-PEG nanoparticles includes following steps:

S1, reacting aspirin with a functionalized ionic liquid of PEG to obtain aspirin-functionalized PEG; and S2, dissolving the aspirin-functionalized PEG in an organic solvent to obtain a mixed solution, dropwise adding the mixed solution into water, followed by ultrasonically centrifugation to obtain a precipitate as the A-PEG nanoparticles.

Figure 16:
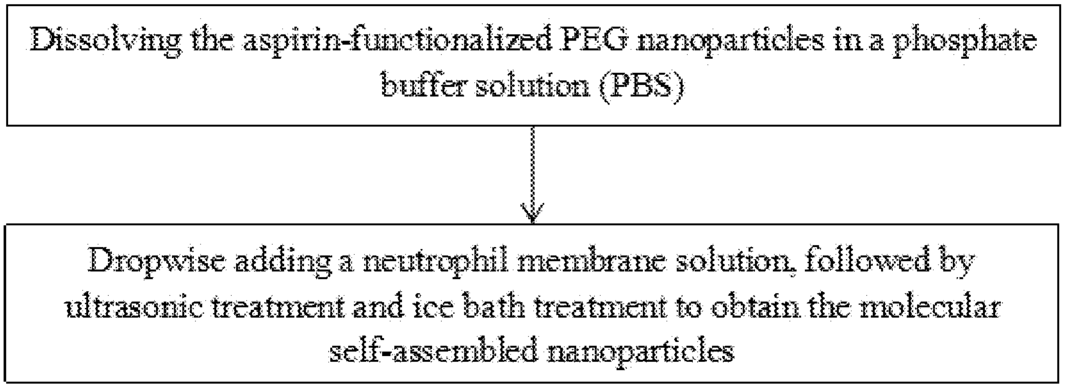
FIG. 16 is a process illustrating a preparation method of molecular self-assembled nanoparticles (PMN-PSAs) of the present application.

FIG. 16 shows a process illustrating a preparation method of molecular self-assembled nanoparticles (PMN-PSAs) of the present application, including following steps:

dissolving the aspirin-functionalized PEG nanoparticles in a phosphate buffer solution (PBS);

then dropwise adding a neutrophil membrane solution, followed by ultrasonic treatment and ice bath treatment to obtain the molecular self-assembled nanoparticles.

Figure 14:
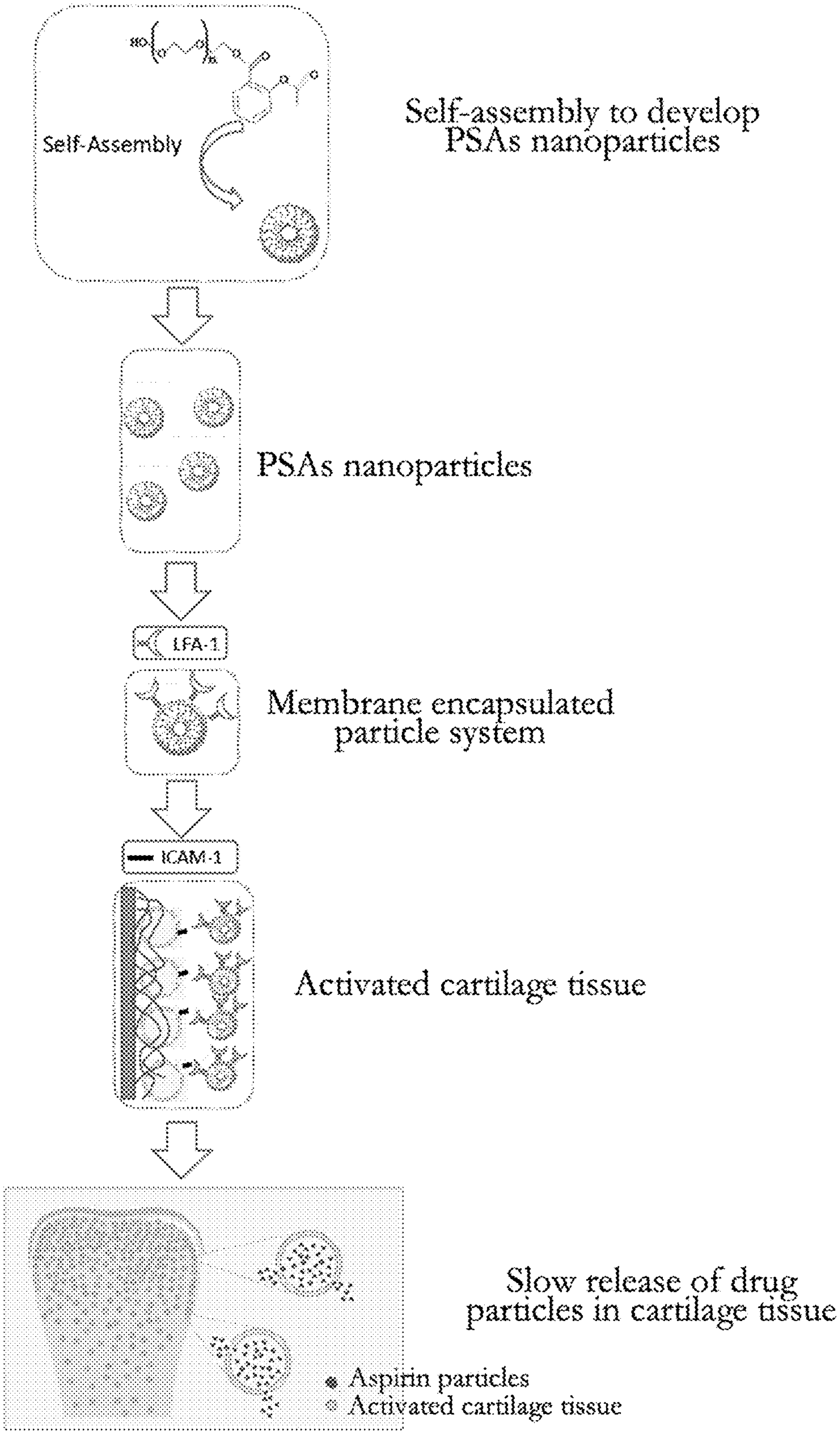
FIG. 14 is a diagram illustrating specific action mode of PMN-PSAs of the present application.

See FIG. 14 for a specific mode of action of PMN-PSAs provided by the present application.

Embodiment 1

Step 1, dissolving 0.05 mg of A-PEG in 1 mL of dimethyl sulfoxide (DMSO) and performing ultrasonic treatment for 30 seconds (s) to obtain an A-PEG/DMSO solution; dropping the A-PEG/DMSO solution into water (a volume ratio of A-PEG/DMSO solution to water is 1:3), performing ultrasonic treatment for 1 min, and then centrifuging at 6,000 rpm for 5 min to prepare polymeric nanoparticle PSAs (A-PEG-Nano-Particles) with uniform particle size and average particle size of 100-200 nano-meters (nm); and step 2, dissolving 0.05 mg PSAs in 1 mL phosphate buffer solution (PBS) and performing ultrasonic treatment for 25 s for fully dissolution to obtain PSAs solution, then dropwise adding PMN membrane solution to the PSAs solution at a constant speed during ultrasonic treatment according to a mass ratio of PSAS:PMN=8:1, and after ultrasonic treatment with 80 Watts (W) power for 1.5 min, taking out and placing in an ice bath for 15 s to obtain polymorphonuclear neutrophils membrane coated self-assembled aspirin particles (PMN-PSAs).

Embodiment 2

Dissolving 0.05 mg polylactic acid-glycolic acid (PLGA) in 1 mL PBS for 25 s for fully dissolution to obtain a PLGA solution, and then adding the PMN membrane solution to the PLGA solution at a constant speed during ultrasonic treatment according to a mass ratio of PLGA:PMN membrane=8:1, after ultrasonic treatment for 1.5 min, taking out and placing in an ice bath for 15 s to obtain polymorphonuclear neutrophils membrane coated self-assembled PLGA (PMN-NPs, NPs stands for neutrophils).

The performance of PSAs and PMN-PSAs prepared in Embodiment 1, and PMN-NPs prepared in Embodiment 2 is verified as follows.

Figure 2:
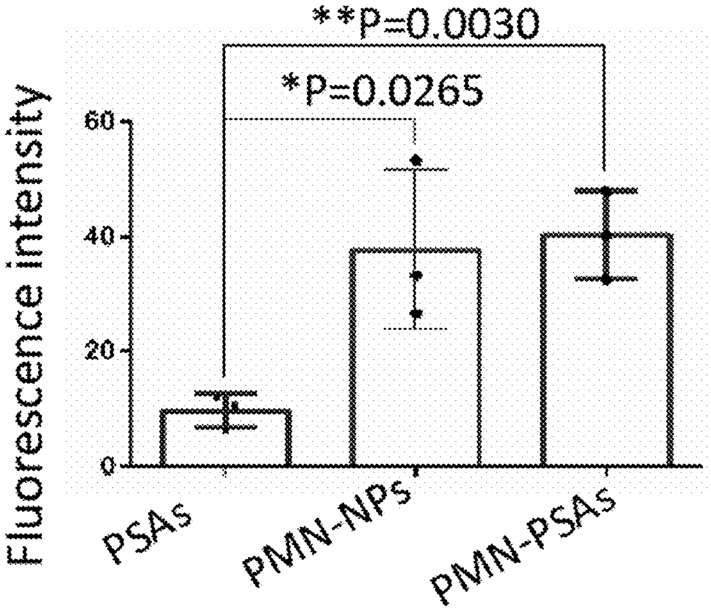
FIG. 2 is a quantitative picture illustrating drug retention of articular chondrocytes.

1. Under the same conditions, aspirin (PSAs), PMN-NPs and PMN-PSAS 100 microliters (μL) of 0.05 mg/mL are injected into the joints of rheumatoid arthritis (RA) model mice respectively, followed by taking materials for frozen section after 48 hours (h); after 4',6-diamidino-2-phenylindole (DAPI) staining, the particles in articular cartilage are observed under laser confocal, with results as shown in FIG. 1; as can be seen form the FIG. 1, the PMN-PSAs are mostly swallowed by chondrocytes, and chondrocytes on articular cartilage surface are more effectively loaded with PMN-PSAs in inflammatory environment. FIG. 2 is a quantitative picture illustrating drug retention of articular chondrocytes, which demonstrates that PMN-PSAs are retained longer at the site of action and at the cartilage site.

Figure 3A:
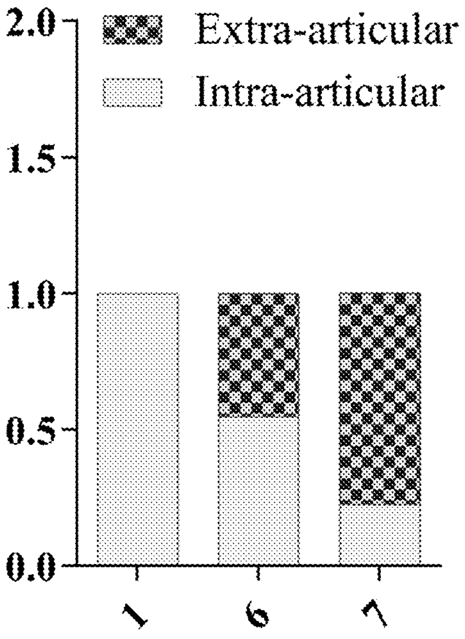
FIG. 3A shows drug retention results and drug release assays for experimental mice of the present application.
Figure 3B:
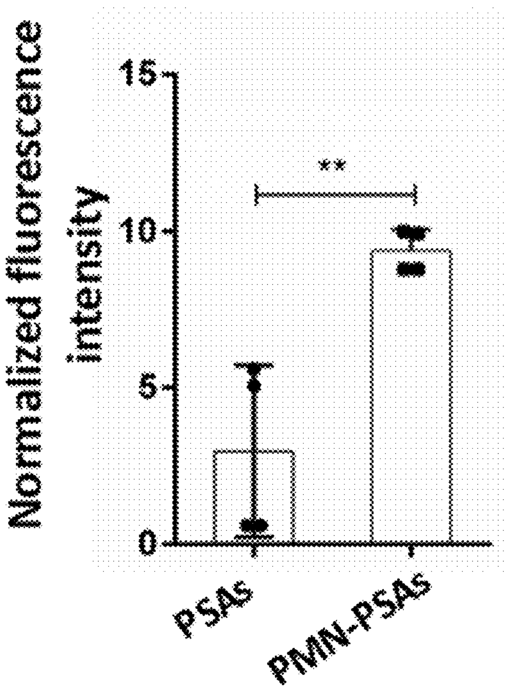
FIG. 3B shows normalized fluorescence intensity of drugs in the experimental mice of the present application.
Figure 3C:
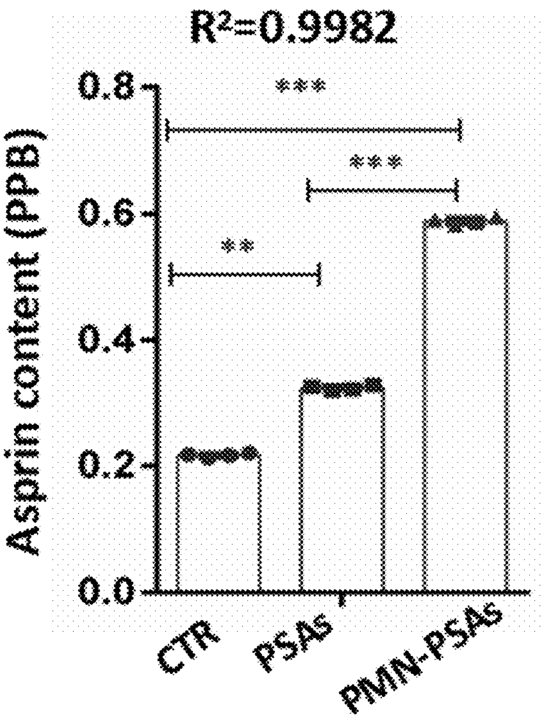
FIG. 3C shows levels of aspirin drug monomer in the joint fluid in the joint cavity of the experimental mice of the present application.

FIG. 3A shows the results under a stereomicroscope after 8 days of topical drugging (PSAs loaded with rhodamine B) at the joints of RA model mice, as indicated by the red fluorescence intensity, there is a significant prolonged retention of PMN-PSAs at the articular cartilage under inflammatory conditions (the drug is not rapidly degraded by the chondrocytes after phagocytosis, but stored in the chondrocytes). Subsequently, the joint fluid (6 days of treatment) in the joint cavity of experimental mice is extracted and tested for aspirin drug monomer content, thereby explaining the gradual process of drug monomer release after chondrocyte phagocytosis, and the rate of drug degradation is (chondrocytes+PSAs>chondrocytes+PMN-NPs>chondrocytes+PMN-PSAs), indicating that chondrocytes+PMN-PSAs act better as a reservoir at the site of joint lesions, i.e., it is efficient in long-term medicinal performance and maintains a balanced inflammatory environment of the body (see FIG. 3B and FIG. 3C).

Figure 4:
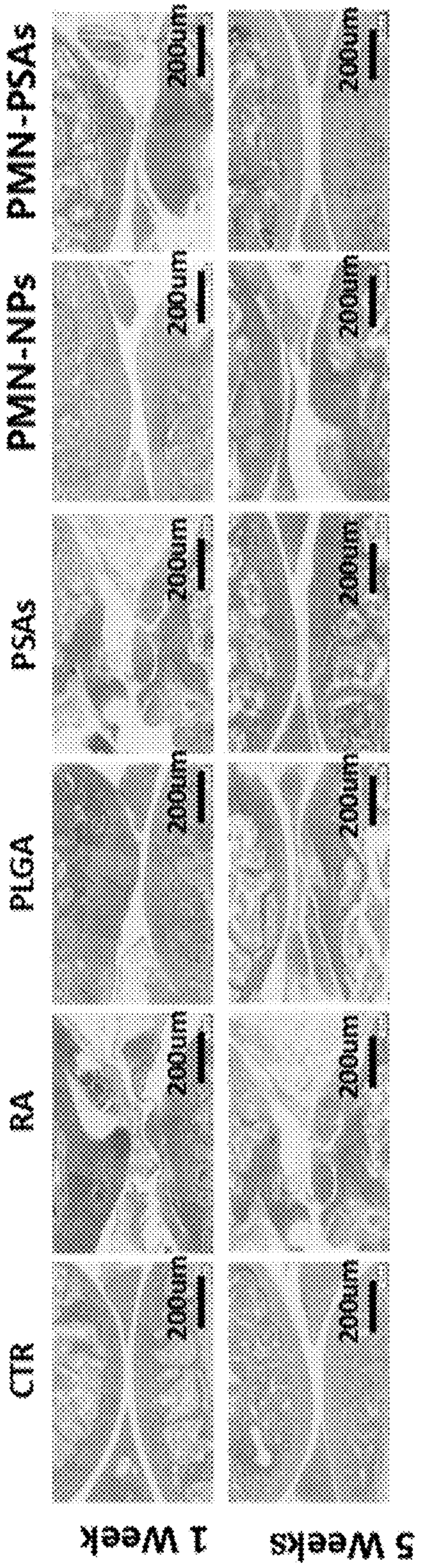
FIG. 4 shows a verification of polymorphonuclear neutrophils membrane coated self-assembled poly salicylic acid (PMN-PSAs) particles prepared by the present application as comparing to other systems in terms of animal therapeutic effect.
Figure 5:
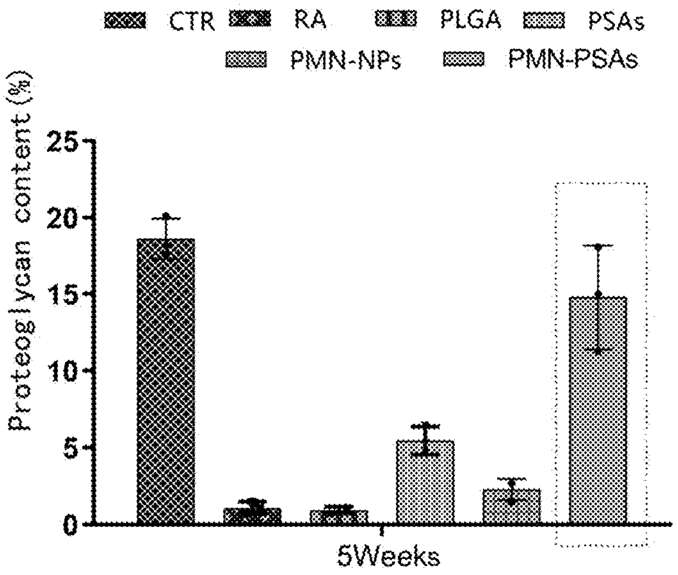
FIG. 5 is a quantitative graph of cartilage bone mass of the present application.
Figure 6A:
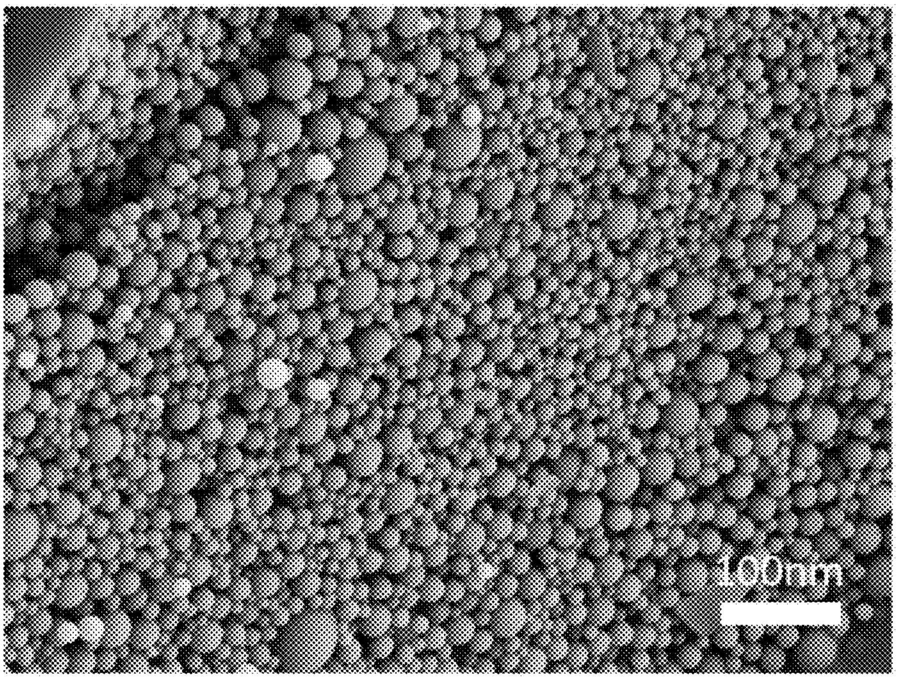
FIG. 6A is a transmission electron microscope diagram of nanoparticles PSAs prepared in Embodiment 1 of the present application.
Figure 6B:
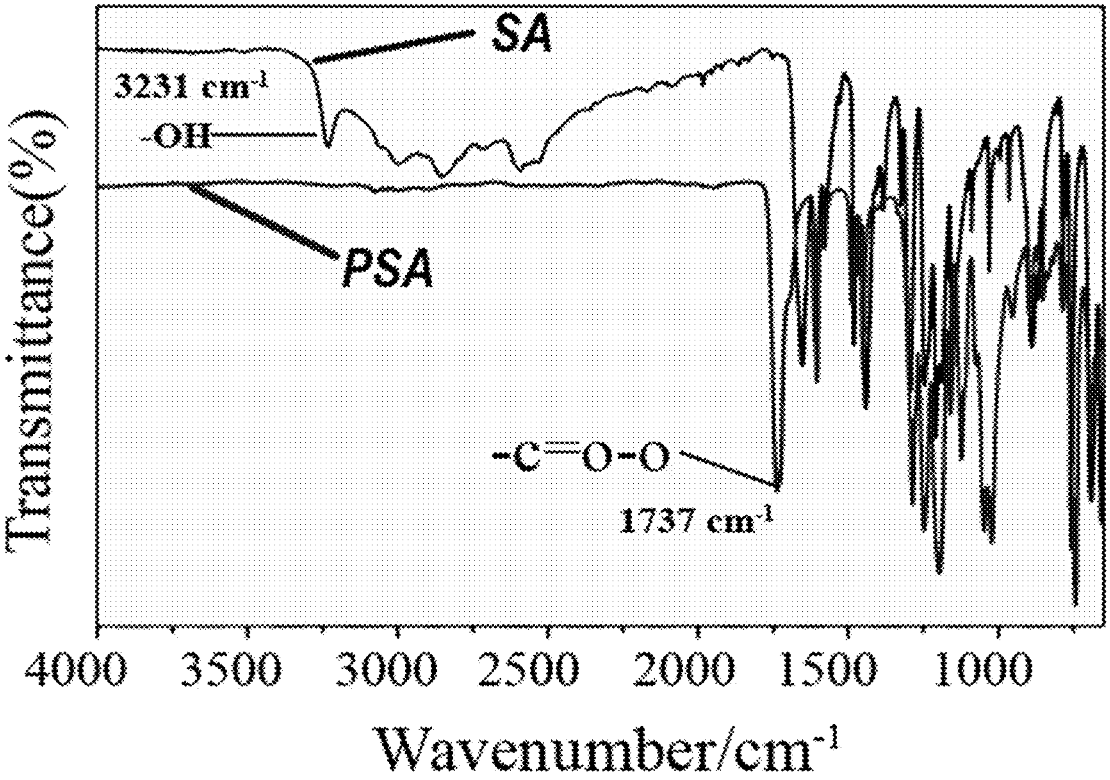
FIG. 6B is an infrared spectrogram of the nanoparticles PSAs prepared in Embodiment 1 of the present application.
Figure 6C:
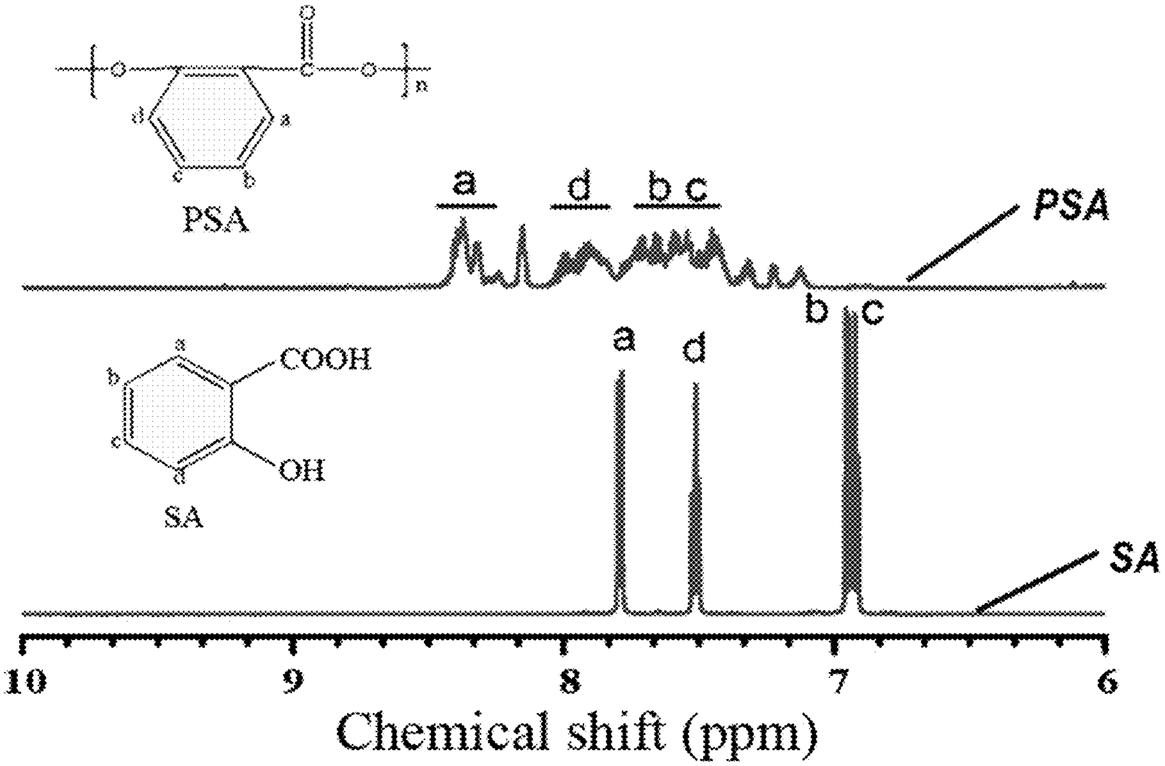
FIG. 6C is a Raman spectrogram of the nanoparticles PSAs prepared in Embodiment 1 of the present application.
Figure 6D:
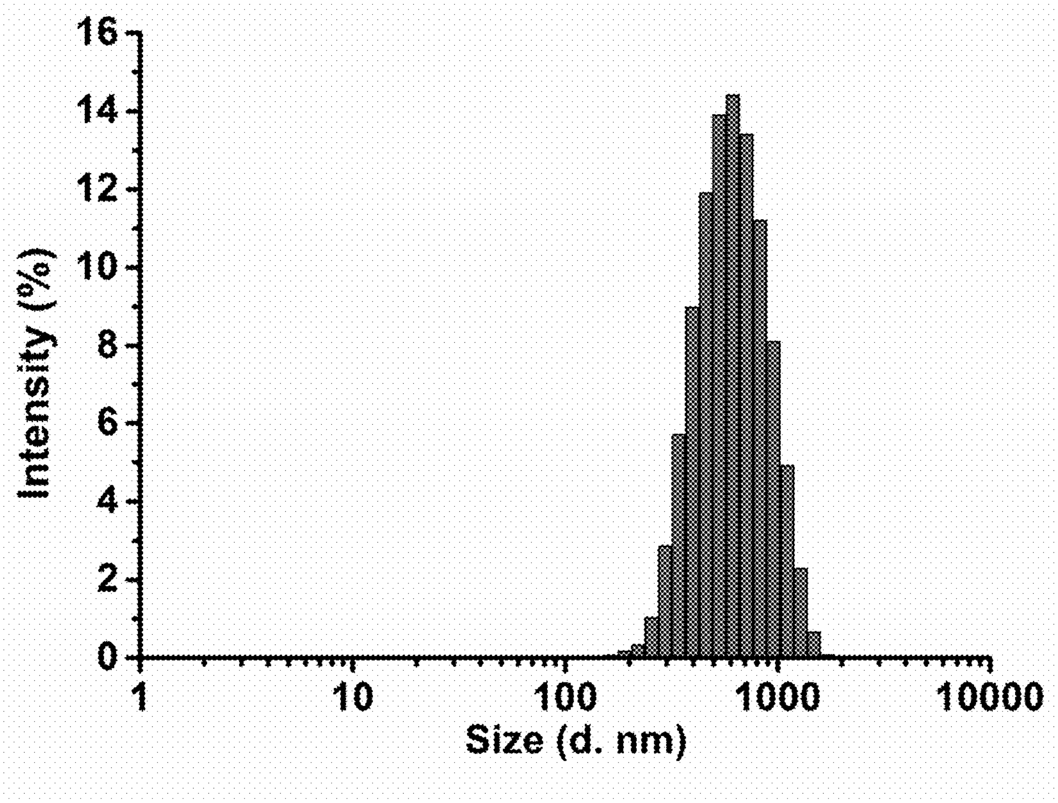
FIG. 6D is a particle size distribution diagram of the nanoparticles PSAs prepared in Embodiment 1 of the present application.
Figure 6E:
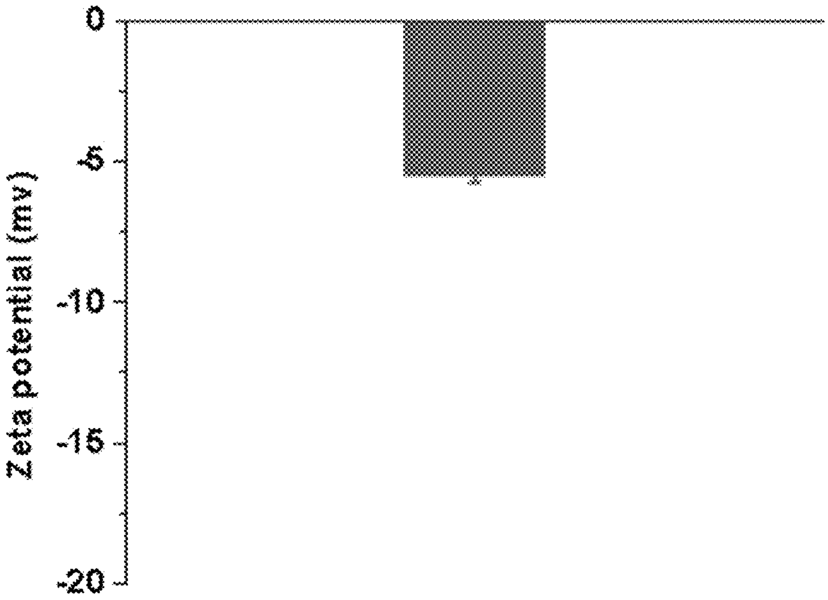
FIG. 6E is a distribution diagram of potential detection of the nanoparticles PSAs prepared in Embodiment 1 of the present application.
Figure 7:
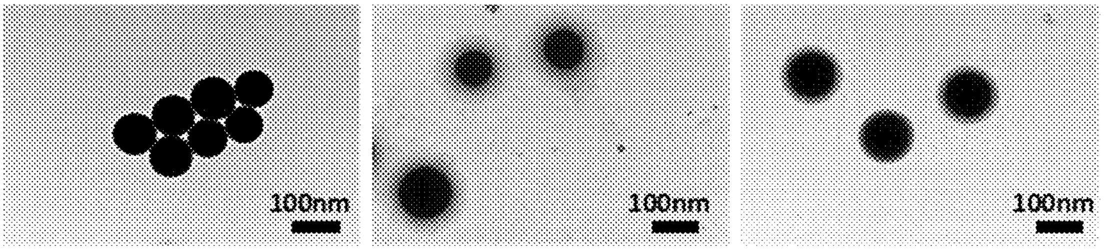
FIG. 7 is a transmission electron microscope diagram of a PMN-PSAs coating system of the present application.
Figure 8:
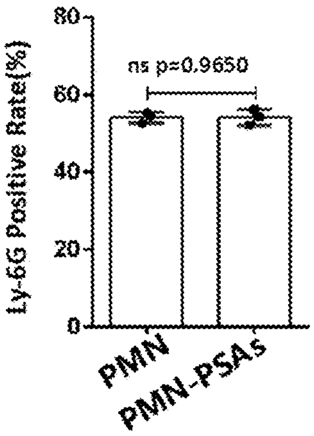
FIG. 8 is a graph illustrating a flow detection of key molecules on a membrane surface of the present application.

2. FIG. 4 (in which SHAM stands for control group, RA stands for rheumatoid arthritis) shows that after RA membrane formation is completed (21st day), medication is started on 21st day, and 150 μL of 0.05 mg/mL of PMN-PSAs is injected once a week. After 5 weeks of continuous treatment, the animal therapeutic effect of the drug system is verified by hematoxylin-eosin (HE) staining of tissue sections, thereby demonstrating the effect of chondrocytes acting as a reservoir (chondrocytes+PMN-PSAs>chondrocytes+PMN-NPs>chondrocytes+PSAs), further demonstrating that the system chondrocytes+PMN-PSAs works more efficiently after storing the drug. The quantification of cartilage bone mass is shown in FIG. 5 (with CTR indicating control, and RA indicating rheumatoid arthritis), which proves that the chondrocyte+PMN-PSAs system is more effective for cartilage repair in RA joints than other systems (chondrocyte+PMN-NPs, chondrocyte+PSAs, etc.).
3. FIGS. 6A-6E are characterization diagrams of nanoparticles PSAs prepared in Embodiment 1 of the present application, in which, FIG. 6A is a transmission electron microscope diagram of nanoparticles PSAs prepared in Embodiment 1 of the present application, FIG. 6B is an infrared spectrogram of nanoparticles PSAs prepared in Embodiment 1 of the present application, FIG. 6C is a Raman spectrogram, FIG. 6D is a particle size distribution diagram of nanoparticles PSAs prepared in Embodiment 1 of the present application, and FIG. 6E is a distribution diagram of potential detection of nanoparticles PSAs prepared in Embodiment 1 of the present application. FIGS. 6A-6E illustrate the successful preparation of nanoparticles PSAs.
4. The mixed solution of Embodiments 1 and 2 with drops of PMN membrane added 2-5 μL before ice bath is dropped onto the copper grid and the particle encapsulation is observed under transmission electron microscopy as shown in FIG. 7, where TEM-Aspirin Nanoparticle (transmission electron microscopy observation of nanoparticles), 1# represents PMN-PSAs, and 2# represents PMN-NPs. FIG. 7 shows that the PMN membrane is encapsulated with nanoparticles PSAs (successful neutrophil membrane encapsulation).
5. The results of PMN outer surface key molecule Ly-6G flow detection with the same concentration of PMN and PMN-PSAs solutions are shown in FIG. 8, which indicates that there is no difference in Ly-6G expression between these two. Thus, it is confirmed that the PMN membrane-encapsulated particles are positively encapsulated on the surface of the particles, rather than haphazardly encapsulated.

The specific receptor LFA-1 present on the PMN membrane itself binds to the ICAM-1 ligand on chondrocytes in the inflammatory state, allowing the PMN-PSAs nanoparticles to target the inflammatory site and to be retained (stored) by chondrocytes.

6. The neutrophil membrane is extracted, and the sediments of neutrophil membrane extraction at 700 rpm, 14,000 rpm, and PMN-PSAs membrane encapsulation system are verified by Western Blot (WB), which proves that LFA-1 protein is abundantly expressed on neutrophil membrane.

Figure 9:
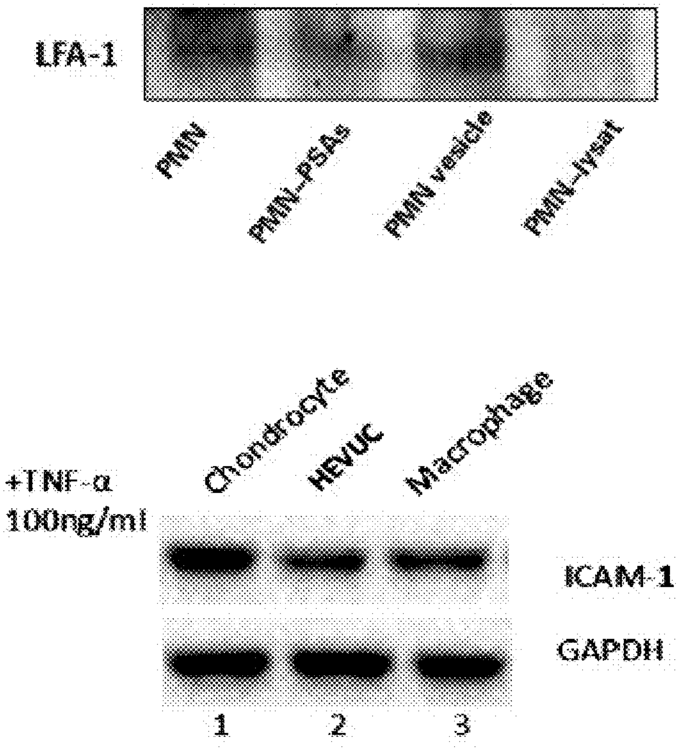
FIG. 9 illustrates a key protein detection experiment of the present application.

Protein blotting experiments with TNF-α (100 ng/mL) activated chondrocytes, vascular endothelial cells (human umbilical vein endothelial cells, HEVUC), and macrophages (abbreviated as Mac) reveal that ICAM-1 expression is higher in activated chondrocytes than in the other two (see FIG. 9 for details). FIG. 9 is a protein detection experiment, which illustrates that activated chondrocytes contain a significant amount of ICAM-1 ligand protein expression, thus demonstrating that chondrocytes are more likely to engulf PMN-PSAs (neutrophil membrane-encapsulated aspirin particles). The integrity of PMN cell membrane surface proteins in PMN-PSAs maintains the physicochemical properties and biological characteristics of neutrophils.

Figure 10:
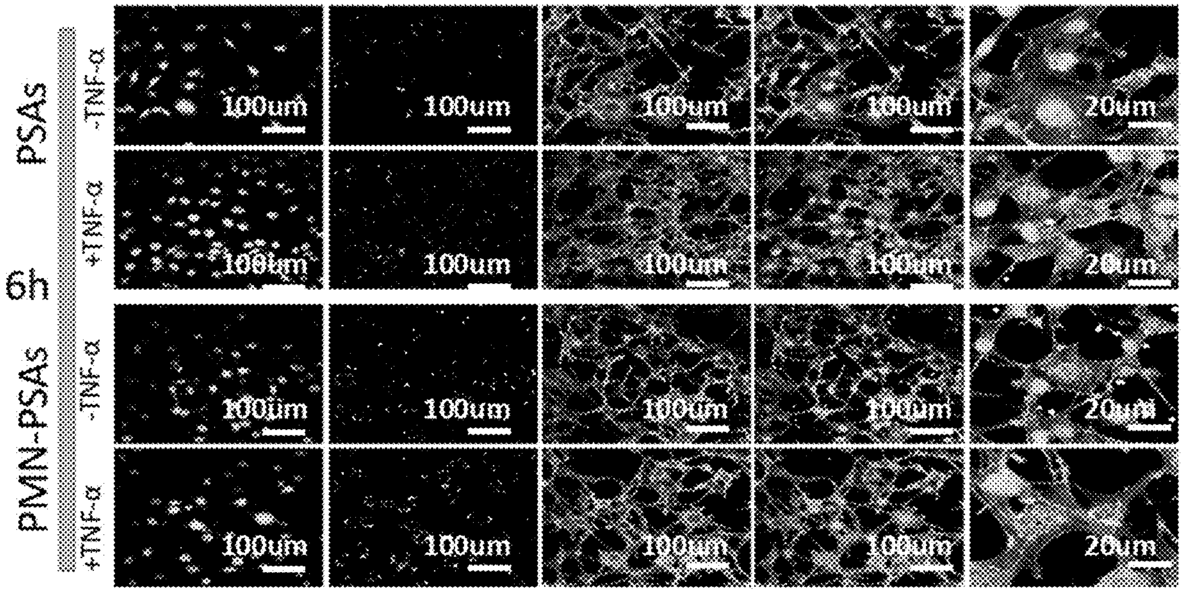
FIG. 10 illustrates a cell uptake experiment of the present application.

TNF-α (100 ng/mL) is used to activate chondrocytes to construct an inflammatory environment in chondrocytes. PSAs, PMN-PSAs are added to the cell culture process for co-incubation of 6 h, and then the cells are fixed and stained. The results of laser confocal reveal that chondrocytes activated in the inflammatory state can engulf PMN-PSAs in large quantities in a short time (6 h) (see FIG. 10 for details). Visual evidence that chondrocytes are prone to ingest PMN-PSAs particles is shown in FIG. 10.

Figure 11A:
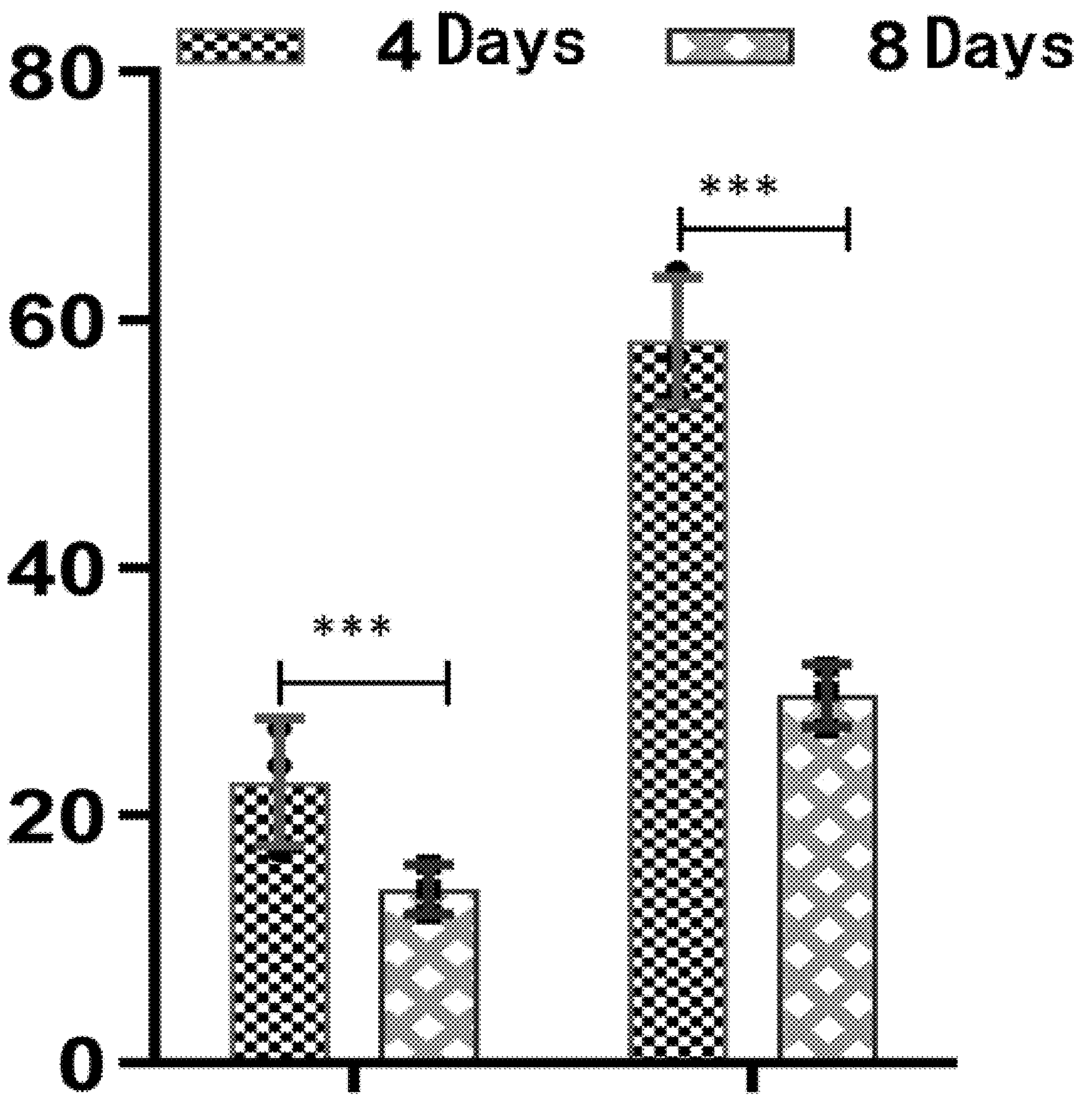
FIG. 11A illustrates observations of the PSAs of the present application with PMN-PSAs under laser confocal at 4 and 8 days of incubation in chondrocytes.
Figure 11B:
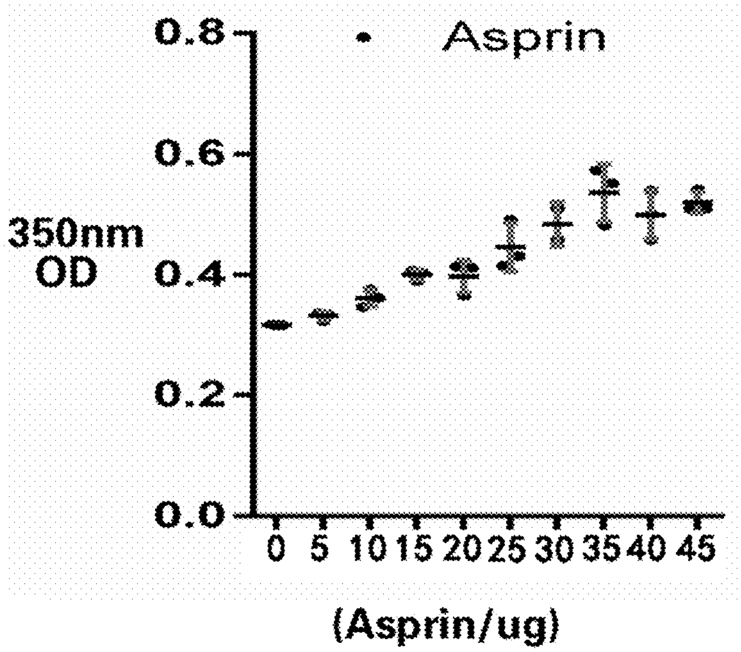
FIG. 11B shows half-life results for PSAs of the present application compared to PMN-PSAs in chondrocytes.

7. The chondrocytes are co-incubated with 10 μL of 0.05 mg/mL of PSAs and PMN-PSAs for 6 h, followed by removal of the medium and washing with PBS for 2-3 times, then added into fresh medium and placed back into the incubator. The results are observed under laser confocal at 4 and 8 days and are shown in FIG. 11A and FIG. 11B, respectively. The results in FIG. 11A and FIG. 11B indicate that PMN-PSAs have a longer half-life, better retention and better ligand binding in chondrocytes compared to PSAs.

Figure 11C:
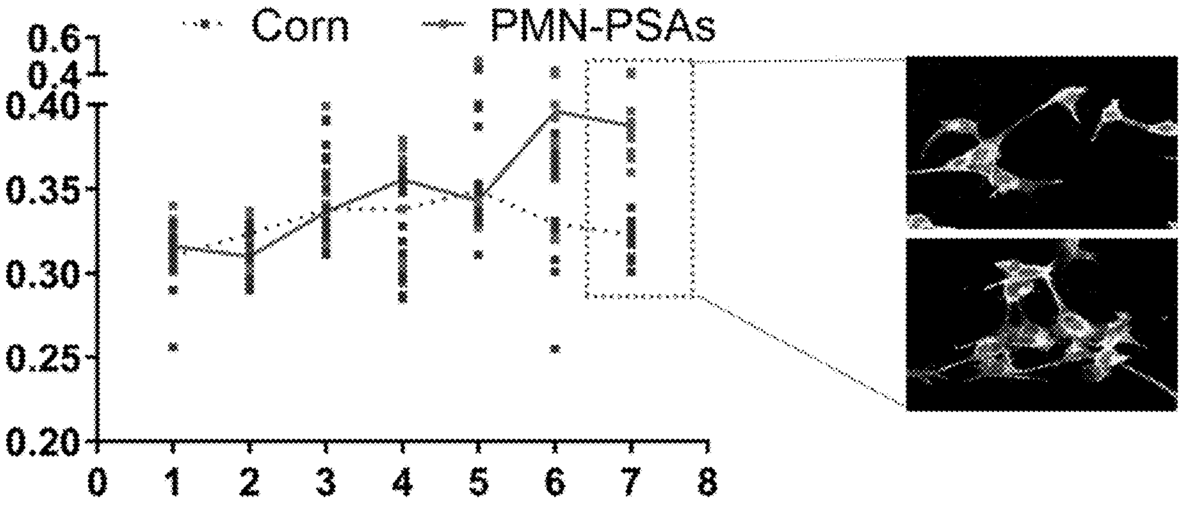
FIG. 11C shows results of different concentrations of PSAs measured by ELISA.

PSAs at different concentrations (0, 5, 10, 15, 20, 25, 30, 35, 40, 45 μg) are detected by enzyme-linked immuno sorbent assay (ELISA) and the results are shown in FIG. 11C, which shows that PSAs are measurable in terms of absorbance value at 350 nm.

Figure 11D:
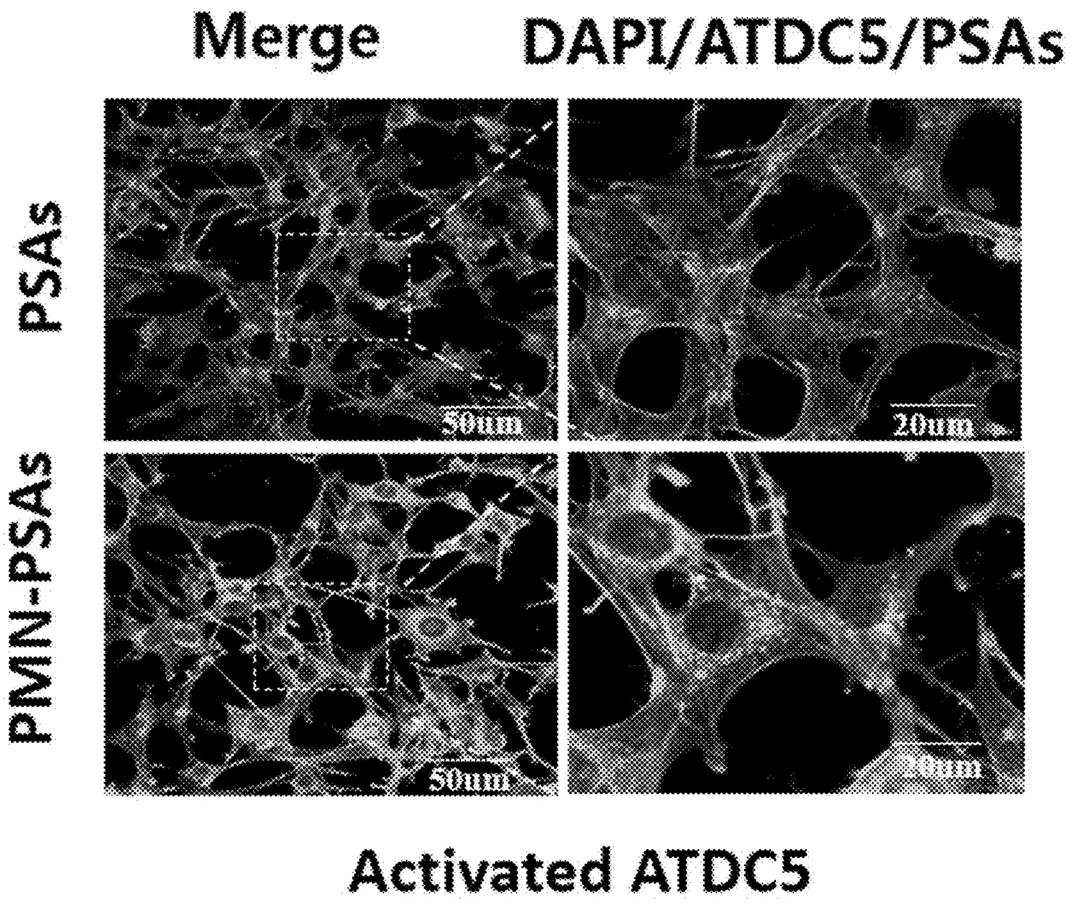
FIG. 11D shows absorbance values of PSAs of the present application with PMN-PSAs after 6 hours incubation in chondrocytes.

The chondrocytes are co-incubated with 10 μL of 0.05 mg/mL of PSAs and PMN-PSAs for 6 h, followed by removal of the medium and washing with PBS for 2-3 times, then added into fresh medium and placed back into the incubator, followed by daily measurement of absorbance values in the supernatant, and the results are shown in FIG. 11D, which also shows that PMN-PSAs have a superior process of release in chondrocytes (between 4-8 days) compared to normal particles, further illustrating the advantages of PMN-PSAs.

Figure 12:
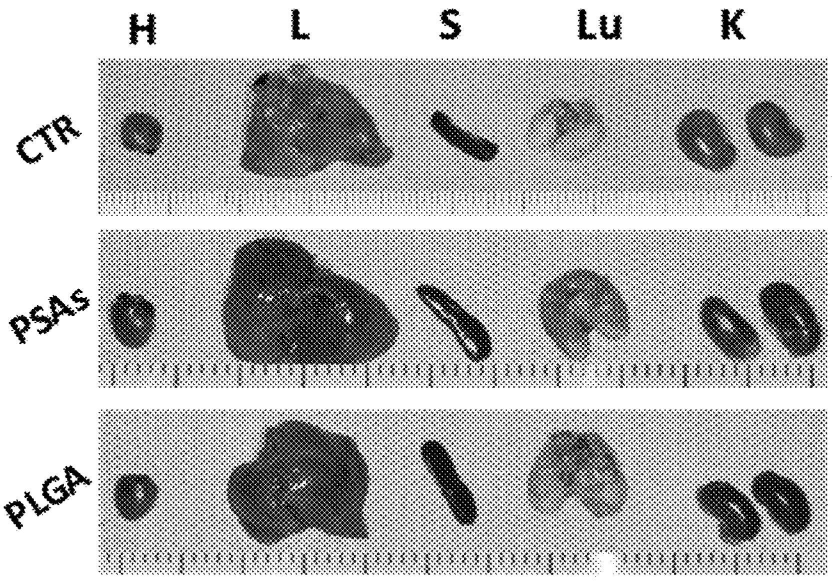
FIG. 12 shows a general observation of the present application in terms of test safety.
Figure 13:
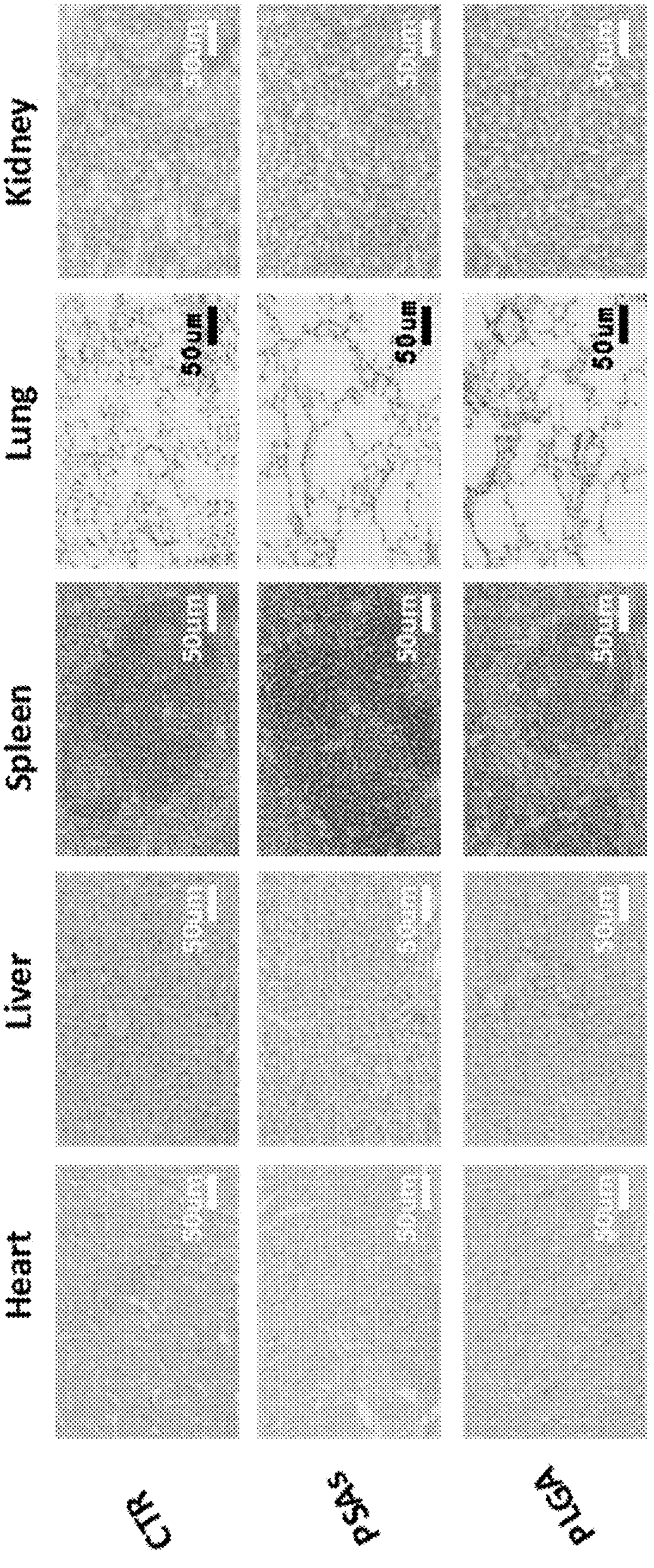
FIG. 13 is a slice observation of the safety test of the present application.

8. After 3 days of drug injection (50 μL 0.05 mg/mL) into the intraperitoneal cavity and joints of the mice, the sections are taken and the gross observations of the main organs are shown in FIG. 12 (CTR denotes control group and the control group is injected with PBS, H denotes heart, L denotes liver, S denotes spleen, Lu denotes lung, and K is kidney). FIG. 12 shows that there is no difference between the experimental group (drug injected group) and the control group. Subsequently, HE staining of the sections of the organs is performed, with results as shown in FIG. 13, which suggests that there is no difference between the groups injected with PSAs, PLGA and CTR, confirming the good biosafety of the nanomedicine synthesized by the present application.

The above described embodiments are only a description of the preferred manner of the present application, not a limitation of the scope of the present application. Without departing from the spirit of the design of the present application, all kinds of deformations and improvements made to the technical schemes of the present application by a person of ordinary skill in the art shall fall within the scope of protection determined by the claims of the present application.

What is claimed is:

1. A method for preparing molecular self-assembled nanoparticles, comprising the following steps:

step 1: dissolving aspirin and polyethylene glycol (PEG) in a mixed solvent of dichloromethane and ethyl acetate or acetone to form an oil phase, emulsifying the oil phase in an aqueous solution to obtain an oil-in-water emulsion, and drying the solvent to obtain aspirin-functionalized PEG;

step 2: dissolving the aspirin-functionalized PEG in a dimethyl sulfoxide (DMSO) solvent to obtain a mixed solution, and dropping the mixed solution into water, followed by centrifugation to obtain aspirin-functionalized PEG nanoparticles; and step 3: dissolving the aspirin-functionalized PEG nanoparticles in a phosphate buffer solution (PBS), then dropwise adding a neutrophil membrane solution, followed by ultrasound and ice bath to obtain the molecular self-assembled nanoparticles.

2. The preparation method according to claim 1, wherein a mass-volume ratio of the aspirin-functionalized PEG nanoparticles to the PBS is 0.05 milligram:1 milliliter.

3. The preparation method according to claim 1, wherein a concentration of the neutrophil membrane solution is 4 milligrams per milliliter.

* * * * *